(12) United States Patent
Partlett et al.

(10) Patent No.: US 8,641,697 B2
(45) Date of Patent: Feb. 4, 2014

(54) STEERABLE CATHETER

(75) Inventors: Matthew Partlett, Allawah (AU); Neil L. Anderson, Roseville (AU); Evan Chong, South Strathfield (AU); Jesse Woolaston, Cremorne (AU)

(73) Assignee: Cathrx Ltd., Homebush Bay, NSW (AU)

( * ) Notice: Subject to any disclaimer, the term of this patent is extended or adjusted under 35 U.S.C. 154(b) by 705 days.

(21) Appl. No.: 11/659,274

(22) PCT Filed: Feb. 18, 2005

(86) PCT No.: PCT/AU2005/000216
§ 371 (c)(1),
(2), (4) Date: Dec. 23, 2008

(87) PCT Pub. No.: WO2006/012668
PCT Pub. Date: Feb. 9, 2006

(65) Prior Publication Data
US 2009/0131865 A1 May 21, 2009

Related U.S. Application Data

(60) Provisional application No. 60/599,720, filed on Aug. 5, 2004.

(51) Int. Cl.
*A61M 25/00* (2006.01)
*A61M 31/00* (2006.01)
*A61M 37/00* (2006.01)

(52) U.S. Cl.
USPC .................. 604/528; 604/523; 604/95.04

(58) Field of Classification Search
USPC .......... 604/525, 528, 530, 529; 600/146–152, 600/136–139
See application file for complete search history.

(56) References Cited

U.S. PATENT DOCUMENTS

| | | | |
|---|---|---|---|
| 4,101,984 A | 7/1978 | MacGregor |
| 4,677,990 A | 7/1987 | Neubauer |
| 5,269,810 A | 12/1993 | Hull et al. |
| 5,299,562 A | 4/1994 | Heckele et al. |
| 5,306,245 A | 4/1994 | Heaven |
| 5,329,923 A | 7/1994 | Lundquist |

(Continued)

FOREIGN PATENT DOCUMENTS

| | | |
|---|---|---|
| AU | 10858/92 A | 8/1992 |
| EP | 0 479 435 A2 | 9/1991 |

(Continued)

OTHER PUBLICATIONS

International Search Report issued Mar. 18, 2005, for PCT Application No. PCT/AU2005/000216, filed Feb. 18, 2005, five pages.

(Continued)

*Primary Examiner* — Nicholas Lucchesi
*Assistant Examiner* — Jenna Zhang
(74) *Attorney, Agent, or Firm* — TraskBritt

(57) ABSTRACT

A steering mechanism for a catheter includes a tubular member defining a passage. The tubular member has a longitudinally extending, bend-enhancing portion formed at a predetermined region of the tubular member. An actuator is received in the passage of the tubular member, with the distal part of the actuator being fastened to a distal part of the tubular member.

39 Claims, 7 Drawing Sheets

(56) References Cited

U.S. PATENT DOCUMENTS

| | | | |
|---|---|---|---|
| 5,454,787 A | 10/1995 | Lundquist | |
| 5,522,874 A | 6/1996 | Gates | |
| 5,834,051 A | 11/1998 | Woloszko et al. | |
| 5,931,862 A | 8/1999 | Carson | |
| 5,976,075 A | 11/1999 | Beane et al. | |
| 6,048,339 A | 4/2000 | Zirps et al. | |
| 6,071,278 A | 6/2000 | Panescu et al. | |
| 6,076,012 A * | 6/2000 | Swanson et al. | 604/21 |
| 6,332,880 B1 * | 12/2001 | Yang et al. | 604/528 |
| 7,178,234 B2 | 2/2007 | Kawasaki et al. | |
| 2002/0161353 A1 * | 10/2002 | Kortelling | 604/528 |
| 2004/0116849 A1 * | 6/2004 | Gardeski | 604/95.04 |
| 2004/0143253 A1 * | 7/2004 | Vanney et al. | 606/41 |

FOREIGN PATENT DOCUMENTS

| | | |
|---|---|---|
| ER | 0 479 435 A3 | 9/1991 |
| JP | 7-255-855 | 10/1995 |
| WO | WO-90/08466 A1 | 8/1990 |
| WO | WO-94/11057 A1 | 5/1994 |
| WO | WO-96/36860 A2 | 11/1996 |
| WO | WO-96/36860 A3 | 11/1996 |
| WO | WO-02/053221 A1 | 7/2002 |

OTHER PUBLICATIONS

Supplementary Partial European Search Report mailed on Feb. 12, 2007, for EP Application No. 01977995 filed on Oct. 19, 2001, five pages.

Notification of the First Office Action for Chinese Patent Application No. 200580026482.7 filed on Feb. 18, 2005, six pages.

EP Examination Report mailed on Oct. 14, 2009, for EP Application No. 05 706 254.9 filed on Feb. 18, 2005, four pages.

Supplemental European Search Report mailed on Apr. 30, 2010, for EP Application No. 10 15 9520, 9 pages.

Japanese Search Report mailed Nov. 2, 2010, for Japanese Patent Application No. P2007-524127, filed Oct. 27, 2010, six pages.

* cited by examiner

STEERABLE CATHETER

CROSS-REFERENCE TO RELATED APPLICATIONS

The present application is a national phase entry under 35 U.S.C. §371 of International Application No. PCT/AU2005/000216, filed Feb. 18, 2005, which claims priority from U.S. Provisional Patent Application No. 60/599,720, filed Aug. 5, 2004, the contents of each of which are incorporated herein by reference in their entirety.

FIELD

This invention relates generally, to a steerable catheter and, more particularly, to a steering mechanism for a catheter and to a steerable catheter including that steering mechanism.

BACKGROUND

Electrophysiology catheters are medical devices used for measuring electrical signals within the heart often in the diagnosis of various arrhythmias. Certain types of these catheters may also be used for treating arrhythmias through ablative techniques.

Generally, to access the region of the heart to be treated, the catheter is inserted through the femoral vein of the patient. The tip of the catheter is steered through the vascular system of the patient to the desired location. Similarly, the catheter tip is steered through the ventricles of the heart to arrive at a desired location.

Steerable catheters have, in the past, often made use of a metal strip or shim contained within a distal end of the catheter as a portion of a steering device. One or more pull wires are connected to the metal strip. Manipulation of these pull wires causes the metal strip to bend to deflect the distal end of the catheter.

Such a design is complex and difficult to manufacture. In particular, these numerous components must be assembled and joined together, typically by hand.

In addition, a catheter lumen often contains a steering device along with other elements such as electrical conductors. Therefore, space within the lumen is at a premium.

SUMMARY

According to a first aspect of the invention, there is provided a steering mechanism for a catheter, the steering mechanism including:
  a tubular member defining a passage, the tubular member having a longitudinally extending, bend-enhancing portion formed at a predetermined region of the tubular member; and
  an actuator received in the passage of the tubular member, a distal part of the actuator being fastened to a distal part of the tubular member.

The bend-enhancing portion may be in the form of a cutaway portion, the cutaway portion subtending an angle greater than 180° of a wall of the tubular member to retain a longitudinally extending web or spine of material of the tubular member.

The actuator may be one of a solid element and a tubular element having a distal end fastened to a distal end of the tubular member, the actuator having a longitudinally extending bend-enhancing portion coincident with the bend-enhancing portion of the tubular member.

In one embodiment, the actuator may be a tubular element having a cutaway portion defining a bend-enhancing portion of the actuator, the cutaway portion subtending an angle greater than 180° of a wall of the tubular element to retain a longitudinally extending web or spine of material of the tubular element. The bend-enhancing portions of the tubular member and of the actuator may be coincident with each other but with the spines of the tubular member and the tubular element lying in opposed relationship relative to each other.

An insert may be arranged between the spines of the tubular member and the tubular element for controlling bending of the tubular member and the tubular element. The insert may be a strip of a resiliently flexible material, such as stainless steel, a suitable plastic material, nitinol, or the like, received between the spines of the tubular member and the tubular element.

In one embodiment, a width dimension of the strip may not exceed an outer diameter of the tubular element.

The mechanism may include a protective arrangement received over the tubular member to inhibit the ingress of foreign material into the tubular member. The protective arrangement may comprise a protective sheath received over the tubular member. The protective arrangement may further comprise a reinforcing structure overlying the bend-enhancing portion of the tubular member and over which the protective sheath is received.

The reinforcing structure may comprise a series of annular members underlying the protective sheath. The annular members may comprise a first, tubular element arranged at a proximal end of the bend-enhancing portion of the tubular member. A series of rings may be arranged distally of the tubular element. It will be appreciated that, the shorter the rings, the greater the degree of flexibility of the bend-enhancing region of the tubular member.

In another embodiment, a width dimension of the strip may exceed an outer diameter of the tubular element.

In this embodiment, the mechanism may include a protective arrangement received over the tubular member to inhibit the ingress of foreign material into the tubular member. The protective arrangement may comprise at least a protective sheath received over the tubular member, the width dimension of the strip imparting a non-circular cross-section to the protective sheath when viewed end-on.

In yet another embodiment, the actuator may be a solid element having a region of reduced cross-section coincident with the bend-enhancing portion of the tubular member.

The tubular member and the actuator may be of a superelastic material, such as, for example, nitinol.

The actuator may be secured to a distal end of the tubular member at an attachment point with a part of the actuator protruding distally of the attachment point, the part of the actuator being shaped into a predetermined shape distally of the attachment point.

The predetermined shape may be in the form of a loop that is cranked distally of the attachment point so that the loop lies in a plane that is transverse to a longitudinal axis of the tubular member.

The part of the actuator being shaped in the predetermined shape may carry radio opaque elements at longitudinally spaced intervals along the length of the part of the actuator.

The mechanism may further comprise:
  a first tubular member;
  a second tubular member received within the passage of the first tubular member, the second tubular member defining a second passage and a distal end of one of the tubular members being secured to the other tubular member at a termination arranged proximally of a distal end of the other tubular member; and an actuator received through the passages of the tubular members with a distal part of the actuator being fastened to a distal part of the other tubular member.

The second tubular member may have a bend-enhancing portion coincident with a bend-enhancing portion of the first tubular member, the bend-enhancing portions of the first tubular member and the second tubular member being arranged proximally of the termination.

The other tubular member may include a second, longitudinally extending bend-enhancing portion, the second, longitudinally extending bend-enhancing portion being arranged intermediate the termination and the distal part of the other tubular member.

The other tubular member may be shaped in the region of the second bend-enhancing portion into a predetermined shape, the shape being able to be altered by manipulation of the actuator. The predetermined shape may be a loop shape, with a diameter of the loop being adjustable by means of the actuator. The other tubular member may be cranked distally of the termination so that the loop lies in a plane extending transversely to a longitudinal axis of the other tubular member.

At least the part of the other tubular member may carry radio opaque elements at longitudinally spaced intervals along the length of the part of the other tubular member. Once again, the radio opaque elements may be positioned in register with, and below, electrodes of an electrode sheath into which the steering mechanism is inserted, in use.

The mechanism may include a protective sheath arranged over the tubular members to inhibit the ingress of foreign material into the tubular members and also to contain the actuator with respect to the tubular members.

According to a second aspect of the invention, there is provided a catheter, which includes:

an elongate element defining a lumen; and a steering mechanism, as described above, received within the lumen.

The elongate element may be secured against rotation relative to the steering mechanism on bending.

The elongate element may be secured against rotation relative to the steering mechanism by being deformed at at least one region of the elongate element in register with the bend-enhancing portion of the tubular member. The elongate element may be deformed by lightly crimping the elongate element where it overlies the bend-enhancing portion of the tubular member.

The elongate element may be crimped at two longitudinally spaced locations of the elongate element to inhibit relative rotation between the elongate element and the steering mechanism.

Optionally, the elongate element may have a non-circular cross-section, when viewed end-on, at least in the region of the elongate element coincident with the bend-enhancing portion of the tubular member of the steering mechanism to inhibit relative rotation between the elongate element and the steering mechanism on bending of the elongate element by the steering mechanism.

According to yet a further aspect of the invention, there is provided a method of fabricating a catheter as described above, the method including:

providing the elongate element; and deforming at least one region of the elongate element in register with the bend-enhancing portion of the steering mechanism to inhibit relative rotation of the elongate element and the steering mechanism on bending.

The method may include deforming the elongate element by crimping the elongate element. Thus, the method may include crimping the elongate element at at least two longitudinally spaced locations on the elongate element.

Further, the method may include crimping the elongate element prior to inserting the steering mechanism into the lumen of the elongate element. The method may include inserting a former into the lumen of the elongate element prior to crimping to limit deformation of the elongate element on being crimped.

DETAILED DESCRIPTION OF EXEMPLARY EMBODIMENTS

Figures 1A, 1B:
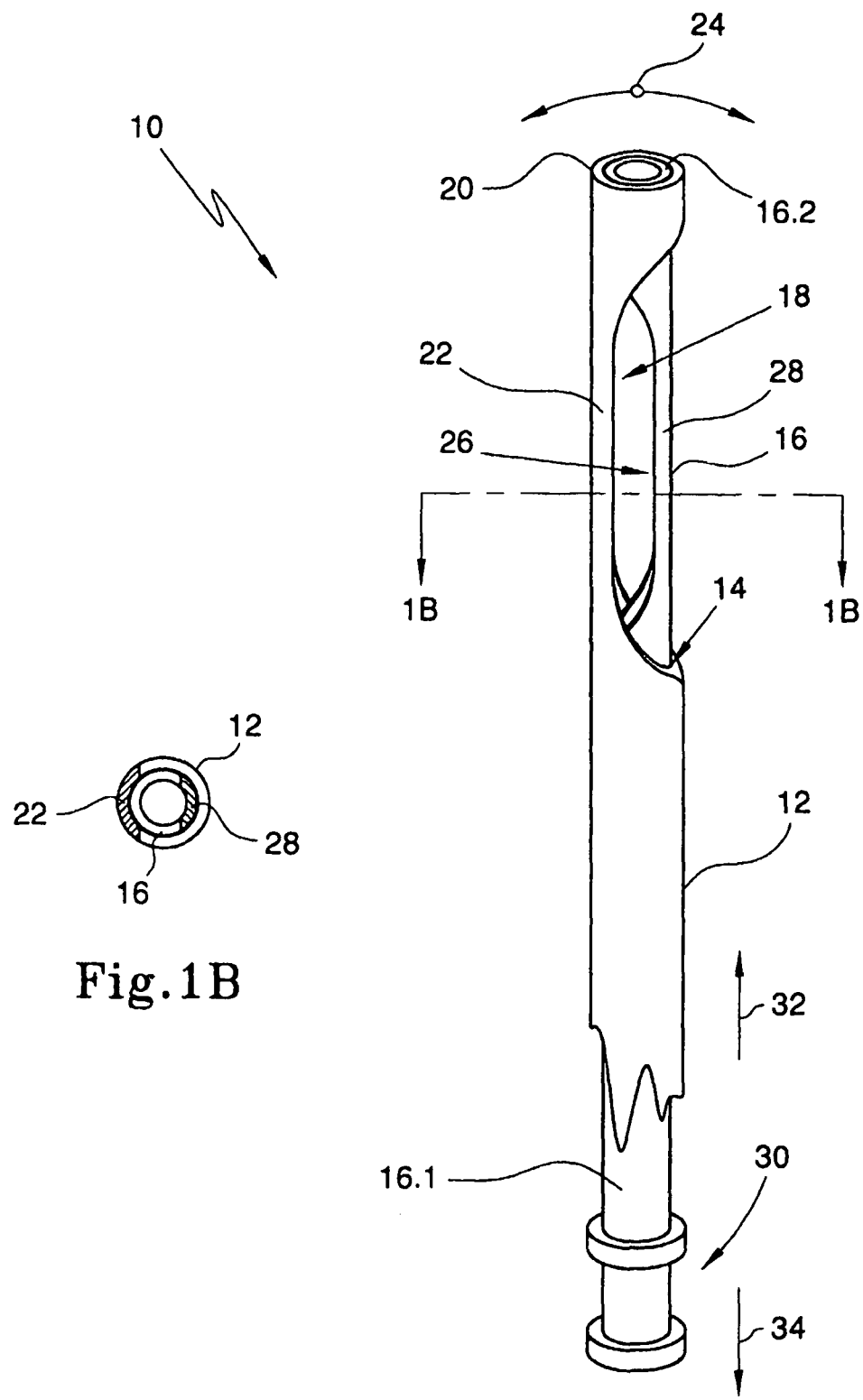
FIG. 1A shows a schematic, perspective view of a steering mechanism, in accordance with an embodiment of the invention, for a catheter.
FIG. 1B shows a cross-sectional view of the steering mechanism of FIG. 1A.

Referring firstly to FIG. 1 of the drawings, an embodiment of a steering mechanism for a catheter is designated generally by the reference numeral 10. The steering mechanism 10 includes a first, outer tubular member 12 defining a passage 14. An actuator 16 is received in the passage 14. In this embodiment, the actuator 16 is also tubular.

The tubular member 12 has a longitudinally extending bend-enhancing portion in the form of a longitudinally extending cutaway portion 18 near a distal end 20 of the tubular member 12. The cutaway portion 18 subtends an angle exceeding 180°. For example, assuming that the tubular member 12 has an outer diameter of approximately 0.66 mm, a web 22 or a wall of the tubular member 12 remains having a width of about 0.25 mm and forms a "hinge" or "spine" about which the distal end 20 of the tubular member 12 can bend in the direction of arrows 24.

The actuator 16 also has a longitudinally extending bend-enhancing, cutaway portion 26 coincident with the cutaway portion 18 of the tubular member 12. However, a web 28 of the tubular actuator 16 lies opposed to the web 22 of the tubular member 12 as shown more clearly in FIG. 1B of the drawings.

The tubular member 12 and the tubular actuator 16 are of any suitable material of construction but, preferably, comprise superelastic alloys, such as nitinol.

A sheath (not shown in this embodiment) overlies the tubular member 12 to contain the actuator 16 with respect to the tubular member 12 and also to inhibit the ingress of foreign material into the passage 14 of the tubular member 12. Although the sheath may be slid onto the steering mechanism 10 or everted and rolled onto the steering mechanism 10, one way to provide a covering is by the use of heat shrink materials or tubing, such as a fluoro-ethylene polymer heat shrink tube that has appropriate strength, lubricity, and biocompatibility properties.

In use, the steering mechanism 10 is inserted into a lumen of an elongate element in the form of an electrode sheath (not shown) of a catheter. A proximal end of the tubular member 12 is affixed to a handle (also not shown) allowing the catheter to be manipulated through the vascular system of a patient. A proximal end of the tubular member 12 is fixed in tension, compression, and rotation relative to the handle of the catheter.

Thus, a proximal end 16.1 of the actuator 16 includes an attachment formation 30 for attachment to a steering control arrangement such as the handle of the catheter.

In this regard, it is to be noted that a distal end 16.2 of the actuator 16 is fixed to the distal end 20 of the tubular member 12 to the extent necessary to move the various tubular members.

When the catheter is to be bent to the left, as viewed in FIG. 1A, the tubular actuator 16 is urged with respect to tubular member 12, in the direction of arrow 32. Conversely, to bend the catheter to the right, as viewed in FIG. 1A, the actuator 16 is pulled in the direction of arrow 34 by the control arrangement of the handle of the catheter.

Figure 2:
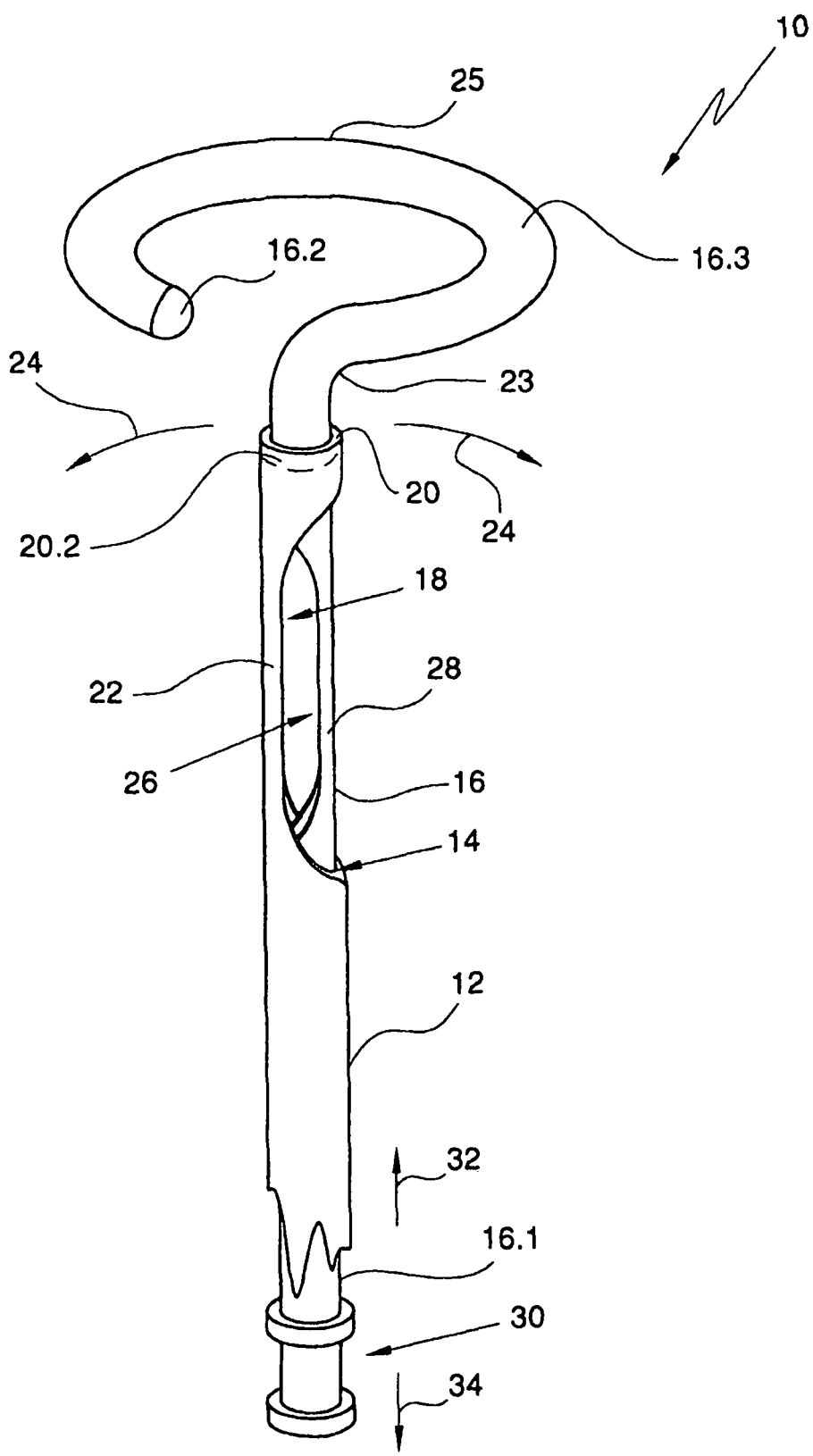
FIG. 2 shows a schematic, perspective view of a steering mechanism, in accordance with another embodiment of the invention, for a catheter.
Figure 4:
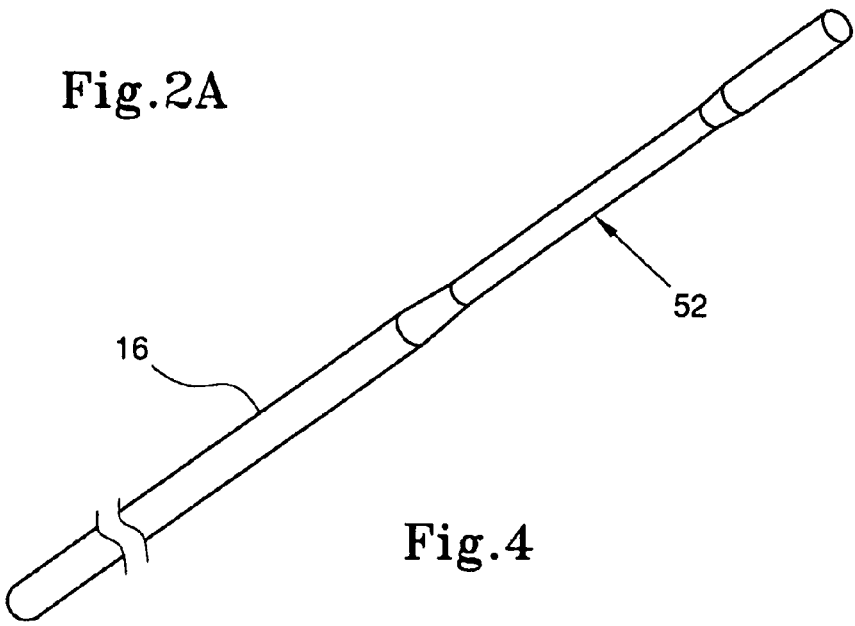
FIG. 4 shows a perspective view of part of another embodiment of an actuator of the steering mechanism.

In the embodiment of the steering mechanism 10 shown in FIG. 2 of the drawings, where, with reference to FIGS. 1A and 1B of the drawings, like reference numerals refer to like parts, the actuator 16 comprises a solid, wire member narrowed in the region of the cutaway portion 18 of the tubular member 12. The narrowed region is either offset with respect to the longitudinal axis of the actuator 16, as shown in FIG. 2 of the drawings, or, instead, the narrowed region is defined by a part 52 of reduced cross-section, as shown in FIG. 4 of the drawings. This part 52 is coincident with the cutaway portion 18 of the tubular member 12 to provide the bend-enhancing region of the steering mechanism 10.

The actuator 16 is secured to the distal end 20 of the tubular member 12 at an attachment point or region 20.2. A part 16.3 of the actuator 16 protrudes distally of the attachment point 20.2. The part 16.3 of the actuator 16 is cranked, as illustrated at 23, distally of the attachment point 20.2. Further, the portion 16.3 distally of the crank 23 is shaped into the form of a predetermined shape, such as a loop 25, that lies in a plane that is generally transverse to a longitudinal axis of the tubular member 12. It will be appreciated that the predetermined shape could take other forms such as, for example, a helix, a spiral, or the like. In this embodiment, the wire actuator 16 is of any suitable material of construction such as, for example, stainless steels, superelastic alloys such as nitinol, or the like. The part 16.3 of the actuator is preformed into the desired shape. Thus, it will be appreciated that, by replacing the steering mechanism 10 having one shape 16.3 of actuator 16 with an actuator 16 having a differently shaped distal part 16.3, different shapes can be imparted to a distal end of the catheter as required by a clinician for particular applications.

Figure 2A:
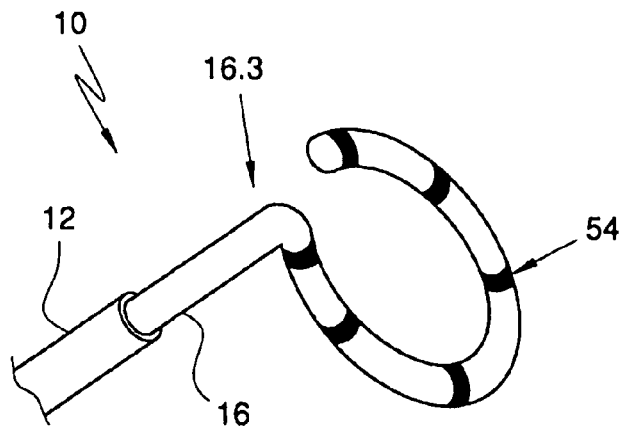
FIG. 2A shows a schematic, perspective view of a part of a variation of the steering mechanism of FIG. 2.

As an enhancement of this embodiment, the part 16.3 of the actuator 16 may carry, at longitudinally spaced intervals along the length of the part 16.3, radio opaque members 54, as shown in FIG. 2A of the drawings. The radio opaque members 54 are applied either as coatings or as short lengths of sleeves having the same length dimensions as electrodes (not shown) on an electrode sheath of the catheter. Further, when the steering mechanism 10 is inserted into the electrode sheath, the radio opaque members 54 underlie the electrodes in register with the electrodes, facilitating positioning of the electrodes by a clinician viewing the catheter via a fluoroscope. When the radio opaque members 54 are in the form of sleeves, they are made from tantalum tubing attached, for example, by crimping the radio opaque members 54 to the part 16.3 of the actuator 16.

Figure 3A:
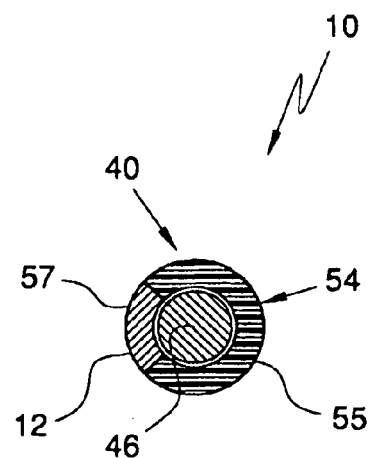
FIG. 3A shows a schematic, cross-sectional view of a part of a variation of the steering mechanism of FIG. 3.
Figure 3:
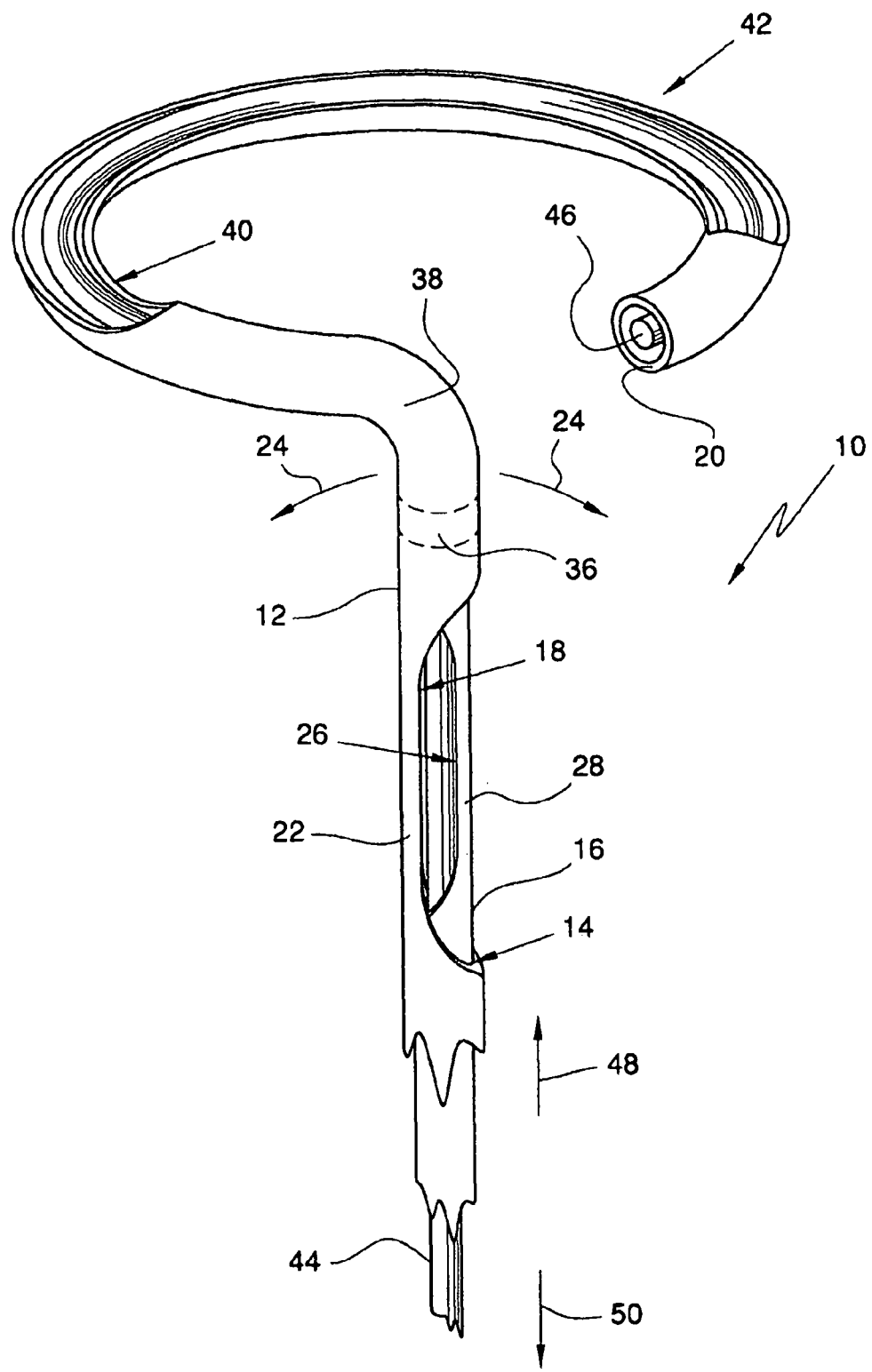
FIG. 3 shows a schematic, perspective view of a steering mechanism, in accordance with still another embodiment of the invention, for a catheter.

Referring now to FIG. 3 of the drawings, yet a further embodiment of a steering mechanism for a catheter is shown. Once again with reference to the previous drawings, like reference numerals refer to like parts, unless otherwise specified.

In this embodiment, the steering mechanism 10 comprises the actuator 16, which is tubular and functions as a first actuator. The actuator 16 terminates at a termination 36 proximally of the distal end 20 of the tubular member 12. The tubular actuator 16 controls bending of the tubular member 12 in the direction of arrows 24 in the same way as described above with reference to FIG. 1A of the drawings. This bending motion is facilitated by the longitudinally extending bend-enhancing cutaway portions 18 and 26 of the tubular member 12 and the actuator 16, respectively, being arranged proximally of the termination 36.

The tubular member 12 is shown to be cranked as illustrated at 38 distally of the termination region 36 to extend further into a loop 42. A second, longitudinally extending, cutaway portion 40 is defined in the tubular member 12 between the cranked region 38 and the distal end 20 of the tubular member 12. The tubular member 12 is preformed with the crank 38 and the loop 42, for example, by heat-setting the material of the tubular member 12.

A further actuator in the form of a length of wire 44 projects through the passages of the tubular member 12 and the tubular actuator 16. A distal end 46 of the wire 44 is fastened to the distal end 20 of the tubular member 12, for example, by crimping the parts together.

The part of the tubular member 12 distally of the termination 36 is steered by manipulation of the tubular actuator 16. Thus, by pushing on the actuator 16, the distal part of the tubular member 12 may be moved to the left, as viewed in FIG. 3 of the drawings. Conversely, by pulling on the tubular actuator 16, the part of the tubular member 12 located distally of the termination 36 is moved to the right.

The diameter of the loop 42 is altered by manipulating the wire 44. Thus, if the wire 44 is pushed in the direction of arrow 48, the diameter of the loop 42 is increased. Conversely, by pulling on the wire 44 in the direction of arrow 50, the diameter of the loop 42 is reduced. It will also be appreciated that pushing and pulling the wire 44 in the direction of the arrows 48 and 50, respectively, may be used to facilitate introduction of a catheter incorporating the steering mechanism 10 into, and manipulation of the catheter through, the vascular system of a patient.

It will be appreciated that the degree to which the distal part of the tubular member 12 can be steered and the degree to which it can be bent is dependent on the shape and dimensions of the cutaway portions 18 and 26 of the tubular member 12 and the tubular actuator 16, respectively. Similarly, the degree to which the radius or diameter of the loop 42 can be altered is governed by the shape and dimensions of the cutaway portion 40 of the tubular member 12 and by the dimensions and material properties of the wire 44.

In FIG. 3A of the drawings, a variation of the steering mechanism 10 of FIG. 3 is shown. In this variation, the part of the tubular member 12 distally of the termination 36 and, more particularly, the loop 42 carries a series of spaced radio opaque elements 54. The radio opaque elements 54 are, once again, either applied as a coating to the outer surface of the tubular member 12 by pad printing or, instead, the radio opaque elements 54 could be cuffs 55 of suitable radio opaque material, such as tantalum. The cuffs 55 are adhesively secured within the cutaway portion 40 and the cuffs 55 are dimensioned so as not to protrude beyond an imaginary circle having a center coincident with a center of the tubular member 12 and having the same outer diameter as that of the tubular member 12. Instead of cuffs 55, the radio opaque elements 54 could also be ovoid to have a part abutting, and being adhesively secured to, a web or spine 57 of material remaining after the cutaway portion 40 of the tubular member 12 has been formed. The cuffs 55, or ovoid elements, as the case may be, are adhesively secured to the tubular member 12 by a suitable adhesive such as a cyano-acrylate adhesive.

A sheath covering the tubular member 12 may, in addition or instead, carry radio opaque elements 54 at longitudinally spaced intervals pad printed on the sheath.

Referring now to FIGS. 5A-5D of the drawings, yet a further embodiment of the steering mechanism 10 is illustrated. Once again, with reference to the previous drawings, like reference numerals refer to like parts, unless otherwise specified.

Figures 5A, 5B, 5C, 5D:
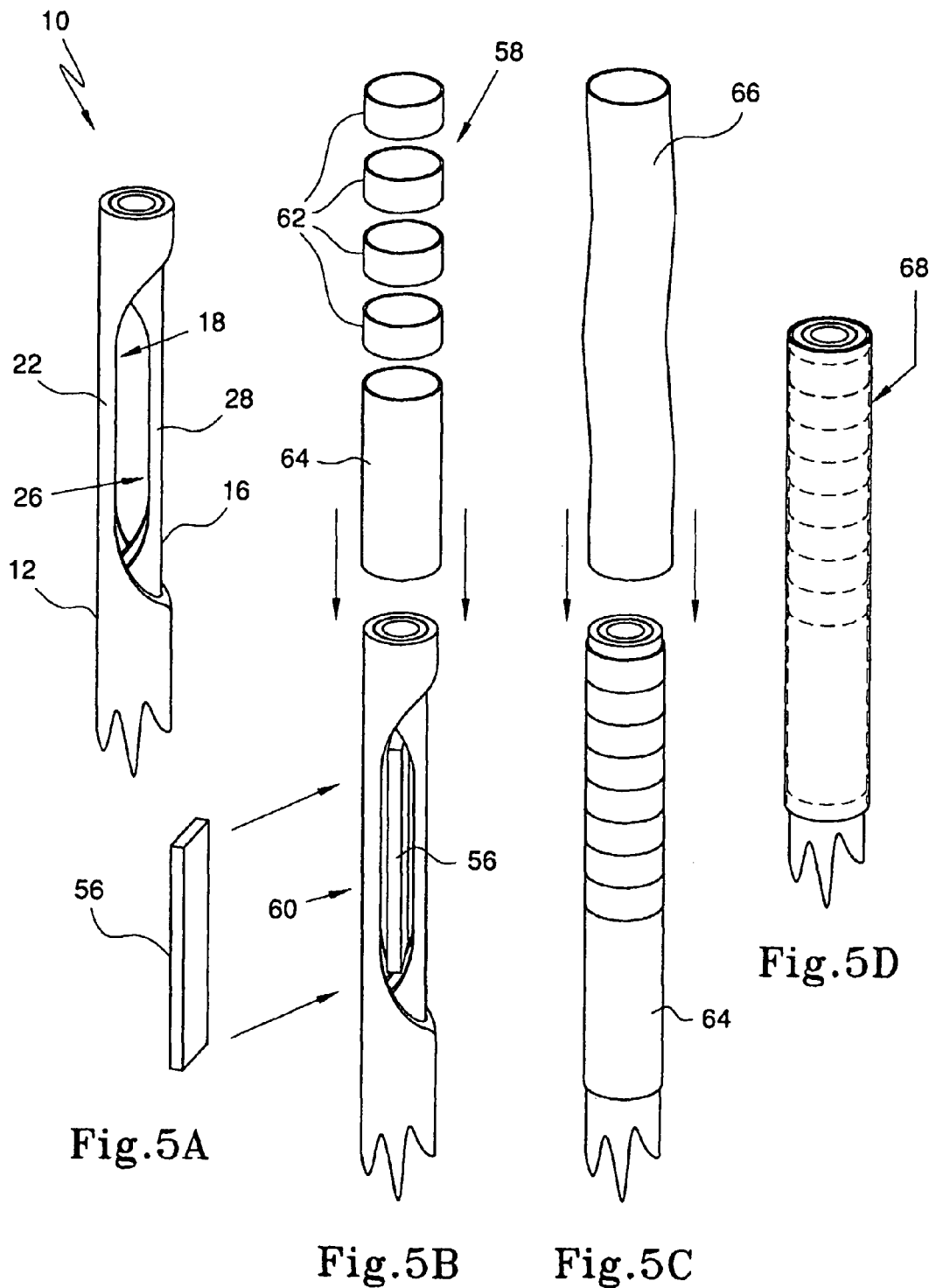
FIGS. 5A-5D show steps in fabricating a steering mechanism, in accordance with yet a further embodiment of the invention, for a catheter.

In this embodiment, a center of support in the form of an insert or shim 56 is inserted between the webs 22 and 28 of the tubular member 12 and the actuator 16, respectively a shown in FIG. 5B of the drawings. The insert 56 acts as a floating center of support and is used to impart a more directional bending behavior to the steering mechanism 10. In this embodiment of the invention, a width of the insert 56 does not exceed an outer diameter of the tubular member 12 and, therefore, is contained within the circumference of the tubular member 12.

To assist in retaining the insert 56 in position relative to the tubular member 12 and the actuator 16, a protective arrangement 58 is applied over the tubular member 12 to overlie and cover a bend-enhancing portion 60 of the tubular member 12 of the steering mechanism 10. The protective arrangement 58 comprises, firstly, a series of containment rings 62 and a slightly longer containment tube 64. The containment rings 62 and the containment tube 64 are applied over the tubular member 12 in the region of the bend-enhancing portion 60. Typically, the rings 62 have a length in the range of 0.5 mm to 1.5 mm and, preferably, about 1 mm. The shorter the length of the rings 62, the greater the flexibility of the steering mechanism 10.

The containment tube 64 fits over the proximal end of the bend-enhancing portion 60 to reduce the likelihood of breaking at the proximal end of the bend-enhancing portion 60. The containment tube 64 limits the amount of bend at the proximal end of the bend-enhancing portion 60 and provides a more gradual bending. The containment tube 64 has a length of at least 10 mm with at least 5 mm overlying the proximal end of the bend-enhancing portion 60. The containment rings 62 and the containment tube 64 are made of short segments of a suitable synthetic plastic material such as a thin-walled rigid polymer tubing, for example, a polyimide tubing.

Once the containment rings 62 and the containment tube 64 have been positioned on the tubular member 12, they are retained in position by a protective sheath 68 in the form of a sleeve 66 of heat shrink material to provide the protective arrangement 58.

Referring now to FIGS. 6 through 10 of the drawings, yet a further embodiment of the steering mechanism is illustrated. In particular, with reference to FIGS. 5A-5D of the drawings, like reference numerals refer to like parts, unless otherwise specified.

Figure 6:
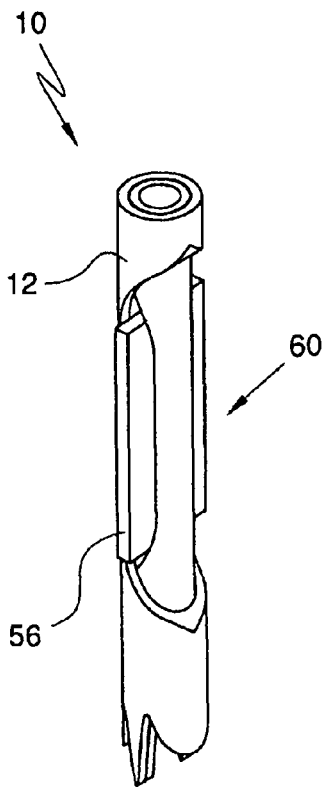
FIG. 6 shows a schematic, perspective view of part of still a further embodiment of a steering mechanism for a catheter.
Figure 7:
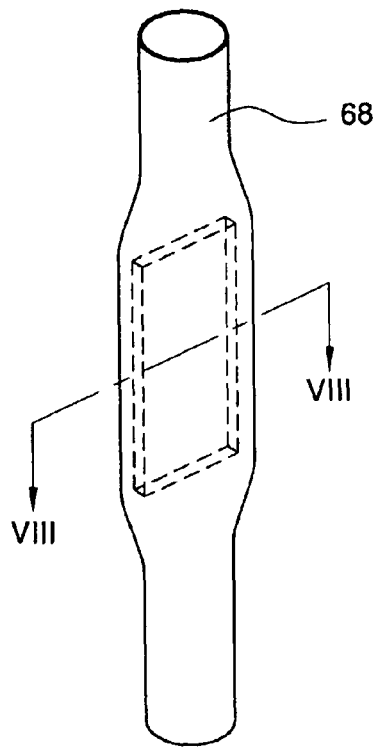
FIG. 7 shows a schematic, perspective view of the steering mechanism of FIG. 6, after application of a protective sheath.
Figure 9:
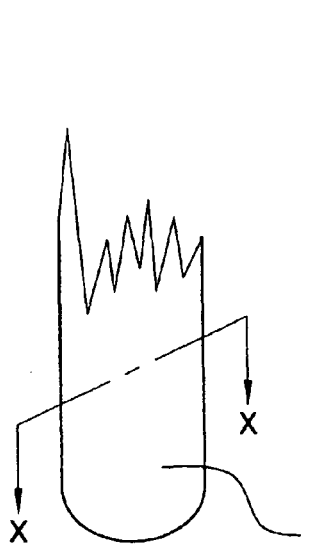
FIG. 9 shows a schematic, perspective view of part of an electrode sheath of a catheter for use with the steering mechanism of FIGS. 6-8.
Figure 8:
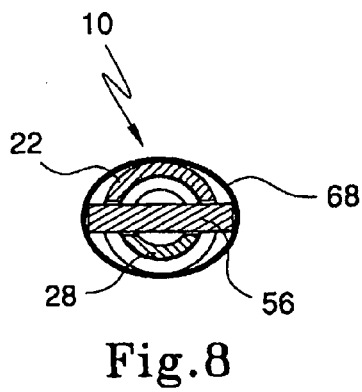
FIG. 8 shows a sectional end view of the steering mechanism of FIG. 7 taken along section line VIII-VIII of FIG. 7.

In this embodiment, and as shown more clearly in FIG. 6 of the drawings, the metal insert 56 has a width dimension exceeding that of an outer dimension of the tubular member 12. As a result, when the protective sheath 68, in the form of a length of heat shrink tube 68 is applied over the bend-enhancing region 60 of the steering mechanism 10, a substantially ovoid cross-section is imparted to the protective sheath 68 as shown more clearly in FIG. 8 of the drawings.

Figure 10:
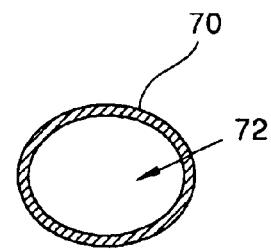
FIG. 10 shows a sectional, end view of the electrode sheath taken along section line X-X of FIG. 9.

Further, in this embodiment, an electrode sheath 70 (FIG. 9) of the catheter has a similar ovoid cross-section, as shown in FIG. 10 of the drawings. This ovoid cross-section extends along the electrode sheath 70 at least for the length of the bend-enhancing portion 60 of the tubular member 12 of the steering mechanism 10. When the steering mechanism 10 is inserted into a lumen 72 of the electrode sheath 70, the ovoid cross-section of the electrode sheath 70 is coincident with the bend-enhancing portion 60 of the steering mechanism 10.

With this arrangement, relative rotation between the steering mechanism 10 and the electrode sheath 70 is inhibited while still permitting a sliding movement, in a longitudinal direction, between the steering mechanism 10 and the electrode sheath 70. Thus, with this configuration of electrode sheath 70 and steering mechanism 10, in-plane, bidirectional steering of the electrode sheath 70 by the steering mechanism 10 is facilitated.

In both of the preceding embodiments, either the tubular member 12 may carry radio opaque elements 54 in the form of pad printed coatings, tubes or cuffs, the metal insert 56 may carry longitudinally spaced radio opaque elements 54 pad printed thereon and/or the protective sleeve 66 or protective sheath 68, as the case may be, may carry pad printed radio opaque elements 54 at longitudinally spaced intervals thereon.

Figure 11:
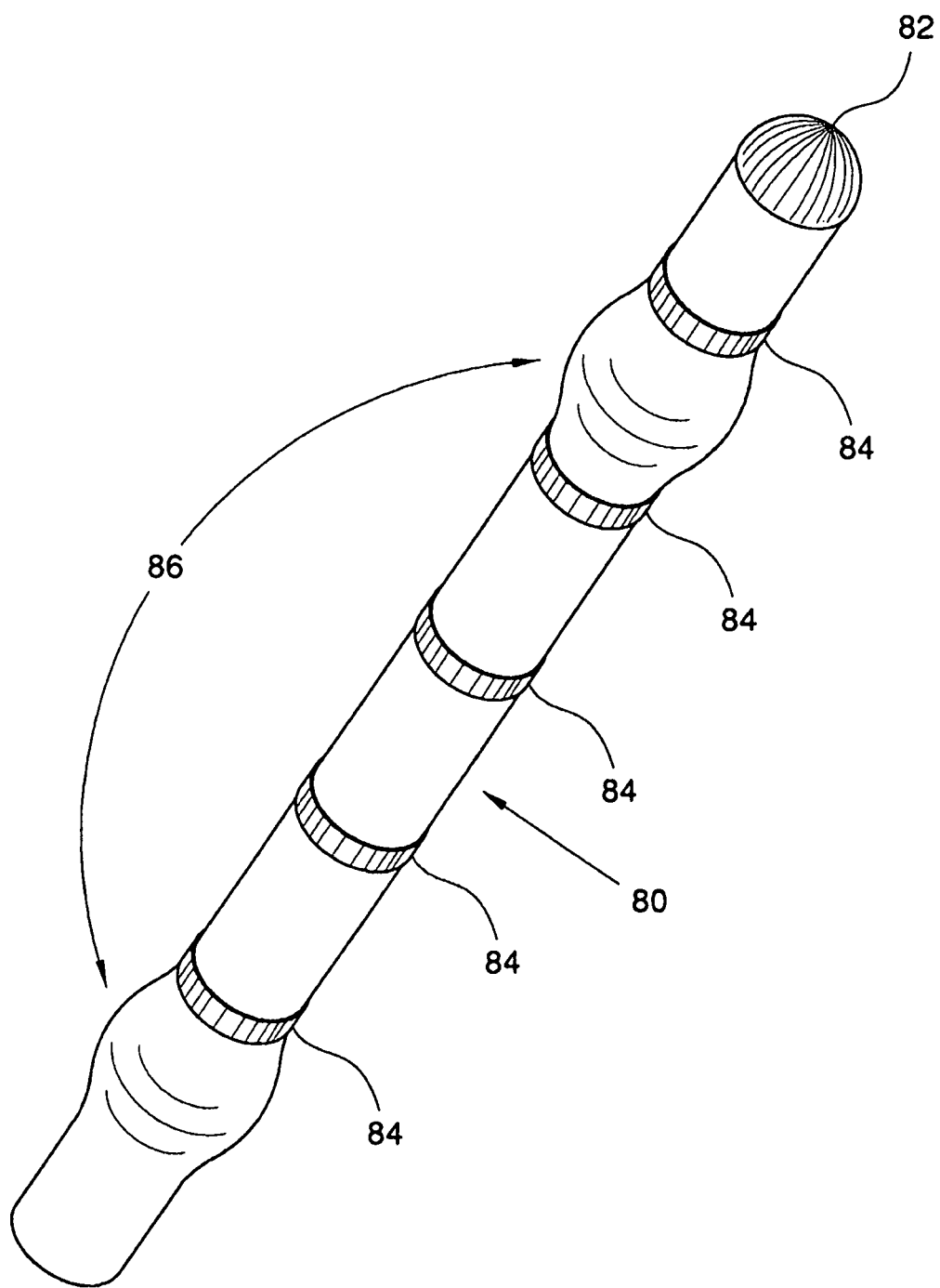
FIG. 11 shows a schematic, perspective view of a distal part of an electrode sheath, in accordance with yet a further embodiment of the invention, for a catheter.

Referring to FIG. 11, an embodiment of an electrode sheath for the catheter is illustrated and is designated generally by the reference numeral 80.

The electrode sheath 80 carries a distal electrode 82 at its distal end and ring electrodes 84 at longitudinally spaced intervals along a distal region of the electrode sheath 80.

In this embodiment, prior to insertion of the steering mechanism 10 (FIG. 1A) into a lumen (not shown) of the electrode sheath 80, the electrode sheath 80 is modified to inhibit relative rotation between the steering mechanism 10 and the electrode sheath 80. More particularly, the electrode sheath 80 is modified by being deformed in its distal region.

To achieve this deformation, a former, in the form of a length of wire (not shown), is inserted into the lumen of the electrode sheath 80. For example, the former could be a 0.66 mm diameter NiTi wire. The wire inhibits excessive deformation of the electrode sheath 80 and facilitates light crimping of the electrode sheath 80.

Once the wire has been inserted into the lumen of the electrode sheath 80, the electrode sheath 80 is deformed by crimping between the first and second ring electrodes 84 and proximally of the proximal ring electrode 84 to form a pair of longitudinally spaced crimped regions 86.

After completion of crimping to form the crimped regions 86, the NiTi wire is removed and the steering mechanism is 10 is inserted into the lumen of the electrode sheath 80.

The crimped regions 86 result in a region of reduced cross-section of the lumen of the electrode sheath 80. The region of reduced cross-section allows the passage of the steering mechanism 10 past the crimped regions 86 but causes sufficient frictional engagement between the electrode sheath 80 and the steering mechanism 10 to inhibit relative rotation between the steering mechanism 10 and the electrode sheath 80 on bending of the steering mechanism 10.

Thus, when the steering mechanism 10 steers the distal region of the electrode sheath 80 in a first direction bending occurs in-plane. When the steering mechanism 10 is manipulated to steer the distal end of the electrode sheath 80 in an opposite direction, the frictional engagement between the steering mechanism 10 and the electrode sheath 80 facilitates in-plane changing of direction of the distal end of the electrode sheath 80. This allows greater control of the distal end of the electrode sheath 80 by a clinician.

It is an advantage of the invention that an accurately steerable catheter may be obtained by using the steering mechanism 10. The steering mechanism 10 is simple to produce. This simplicity results in a comparatively lower cost steering mechanism. Still further, the steering mechanism 10 may be tailored to achieve varying degrees of flexibility by appropriate shaping of the cutaway portions 18, 26, and 40.

It is yet a further advantage of the invention that a steering mechanism 10 is easily formed into a loop. Such a loop allows ablation to be effected at an ostium of a pulmonary vein using a catheter incorporating the steering mechanism 10. In other words, by adjusting the configuration of each of the cutaway portions 18, 26, and 40, large variations in deflection can be obtained in multiple planes as well as varying sizes of loops. Still further, a range of steering mechanisms 10 can be provided with differing distal shapes. A clinician can select the steering mechanism of the required shape to impart that shape to the electrode sheath to enable the clinician to perform a desired function. This further improves the versatility of a modular catheter system including the steering mechanism.

It will be appreciated by persons skilled in the art that numerous variations and modifications may be made to the devices as shown in the specific embodiments without departing from the spirit or scope of the broad description. The disclosure, therefore, is to be considered in all respects as illustrative and not restrictive.

The claims defining the invention are as follows:

1. A steering mechanism for a catheter, the steering mechanism including:
    a tubular member defining a passage, the tubular member having a longitudinally extending, continuous, cutaway, bend-enhancing portion formed at a predetermined region of the tubular member to enhance bending at the region; and
    an actuator comprising a tubular element received in the passage of the tubular member, a distal part of the tubular element being fastened to a distal part of the tubular member, a proximal end of the tubular element configured to extend to a handle of the catheter, the actuator being positioned co-axially within the passage of the tubular member, the actuator having a longitudinally extending bend-enhancing portion coincident with the longitudinally extending, continuous, cutaway, bend-enhancing portion of the tubular member, and the longitudinally extending bend-enhancing portion of the actuator being substantially the same length as the longitudinally extending, continuous, cutaway, bend-enhancing portion of the tubular member, wherein manipulation of the actuator causes bending of the actuator and tubular member at their coincident bend-enhancing portions, the actuator remaining wholly contained within the tubular member at the bend-enhancing portions upon the bending.

2. The mechanism of claim 1, wherein the longitudinally extending, continuous, cutaway, bend-enhancing portion subtends an angle greater than 180 degrees of a wall of the tubular member to retain a longitudinally extending web or spine of material of the tubular member.

3. The mechanism of claim 2, wherein the actuator has a longitudinally extending, continuous, cutaway portion defining the longitudinally extending bend-enhancing portion of the actuator, the longitudinally extending, continuous, cutaway portion of the actuator subtending an angle greater than 180 degrees of a wall of the tubular element to retain a longitudinally extending spine of material of the tubular element.

4. The mechanism of claim 3, wherein the spines of material of the tubular member and the tubular element lie in an opposed relationship relative to each other.

5. The mechanism of claim 4, wherein an insert is arranged between the spines of material of the tubular member and the tubular element for controlling bending of the tubular member and the tubular element.

6. The mechanism of claim 5, wherein the insert is a strip of a resiliently flexible material received between the spines of material of the tubular member and the tubular element.

7. The mechanism of claim 6, wherein a width dimension of the strip does not exceed an outer diameter of the tubular element.

8. The mechanism of claim 6, wherein a width dimension of the strip exceeds an outer diameter of the tubular element.

9. The mechanism of claim 8, further comprising a protective arrangement received over the tubular member to inhibit an ingress of foreign material into the tubular member.

10. The mechanism of claim 9, wherein the protective arrangement comprises at least a protective sheath received over the tubular member, the width dimension of the strip imparting a non-circular cross-section to the protective sheath when viewed end-on.

11. The mechanism of claim 1, further comprising a protective arrangement received over the tubular member to inhibit an ingress of foreign material into the tubular member.

12. The mechanism of claim 11, wherein the protective arrangement comprises a protective sheath received over the tubular member.

13. The mechanism of claim 12, wherein the protective arrangement further comprises a reinforcing structure overlying the longitudinally extending, continuous, cutaway, bend-enhancing portion of the tubular member and over which the protective sheath is received.

14. The mechanism of claim 13, wherein the reinforcing structure comprises a series of annular members underlying the protective sheath.

15. The mechanism of claim 1, wherein the tubular member and the actuator comprise a superelastic material.

16. The mechanism of claim 1, wherein:
    the tubular member is a first tubular member;
    the actuator is a first actuator, the tubular element of the first actuator received within the passage of the first tubular member; and
    the tubular element of the first actuator defines a second passage and a distal end of one of the tubular member and the tubular element being secured to the other of the tubular member and the tubular element at a termination arranged proximally of a distal end of the other of the tubular member and the tubular element, wherein the mechanism comprises a further actuator received through the passages of the tubular member and the tubular element with a distal part of the further actuator being fastened to a distal part of the other of the tubular member and the tubular element.

17. The mechanism of claim 16, wherein the other of the tubular member and the tubular element includes a second, longitudinally extending bend-enhancing portion, the second, longitudinally extending bend-enhancing portion being arranged intermediate the termination and the distal part of the other of the tubular member and the tubular element.

18. The mechanism of claim 17, wherein the other of the tubular member and the tubular element is shaped in the region of the second, longitudinally extending bend-enhancing portion into a predetermined shape, the shape being able to be altered by manipulation of the further actuator.

19. The mechanism of claim 18, wherein the predetermined shape is a loop shape, a diameter of the loop being adjustable by the further actuator.

20. The mechanism of claim 19, wherein the other of the tubular member and the tubular element is cranked distally of the termination so that the loop lies in a plane extending transversely to a longitudinal axis of the other tubular member.

21. The mechanism of claim 20, wherein at least part of the other of the tubular member and the tubular element carries radio opaque elements at longitudinally spaced intervals along the length of the part of the other of the tubular member and the tubular element.

22. The mechanism of claim 16, further including a protective sheath arranged over the tubular member and the tubular element to inhibit an ingress of foreign material into the tubular member and the tubular element and also to contain the further actuator with respect to the tubular member and the tubular element.

23. A catheter, including:
an elongate element defining a lumen; and
a steering mechanism received within the lumen, the steering mechanism including:
a tubular member defining a passage, the tubular member having a longitudinally extending, continuous, cutaway, bend-enhancing portion formed at a predetermined region of the tubular member to enhance bending at the region; and
an actuator received in the passage of the tubular member, the actuator being a unitary, substantially solid element positioned co-axially within the passage of the tubular member, the actuator having a bend-enhancing portion including a continuous region of reduced, uniform cross-section taken along a longitudinal length of the actuator, and the bend-enhancing portion of the actuator being coincident with the longitudinally extending, continuous, cutaway, bend-enhancing portion of the tubular member, wherein manipulation of the actuator causes bending of the actuator and tubular member at their coincident bend-enhancing portions, and the actuator remaining wholly contained within the tubular member at the bend-enhancing portions upon the bending.

24. The mechanism of claim 23, wherein the actuator is secured to a distal end of the tubular member at an attachment point with a part of the actuator protruding distally of the attachment point, the part of the actuator being shaped into a predetermined shape distally of the attachment point.

25. The mechanism of claim 24, wherein the predetermined shape is in the form of a loop that is cranked distally of the attachment point so that the loop lies in a plane that is transverse to a longitudinal axis of the tubular member.

26. The mechanism of claim 24, wherein the part of the actuator carries radio opaque elements at longitudinally spaced intervals along the length of the part of the actuator.

27. The catheter of claim 23, wherein the elongate element is secured against rotation relative to the steering mechanism on bending.

28. The catheter of claim 27, wherein the elongate element is secured against rotation relative to the steering mechanism by being deformed at at least one region of the elongate element in register with the longitudinally extending, continuous, cutaway, bend-enhancing portion of the tubular member.

29. The catheter of claim 28, wherein the elongate element is deformed by crimping the elongate element where the elongate element overlies the longitudinally extending, continuous, cutaway, bend-enhancing portion of the tubular member.

30. The catheter of claim 28, wherein the elongate element is crimped at two longitudinally spaced locations of the elongate element to inhibit relative rotation between the elongate element and the steering mechanism.

31. The catheter of claim 27, wherein the elongate element has a non-circular cross-section, when viewed end-on, at least in that region of the elongate element coincident with the longitudinally extending, continuous, cutaway, bend-enhancing portion of the tubular member of the steering mechanism to inhibit relative rotation between the elongate element and the steering mechanism on bending of the elongate element by the steering mechanism.

32. A method of fabricating a catheter comprising an elongate element defining a lumen; and a steering mechanism received within the lumen, the steering mechanism including a tubular member defining a passage, the tubular member having a longitudinally extending, continuous, cutaway, bend-enhancing portion formed at a predetermined region of the tubular member to enhance bending at the region; and an actuator comprising a tubular element received in the passage of the tubular member, a distal part of the tubular element being fastened to a distal part of the tubular member, the actuator being positioned co-axially within the passage of the tubular member, a proximal end of the tubular element of the actuator configured to extend to a handle of the catheter, the actuator having a longitudinally extending bend-enhancing portion coincident with the longitudinally extending, continuous, cutaway, bend-enhancing portion of the tubular member, and the longitudinally extending bend-enhancing portion of the actuator being substantially the same length as the longitudinally extending, continuous, cutaway, bend-enhancing portion of the tubular member, wherein manipulation of the actuator causes bending of the actuator and tubular member at their coincident bend-enhancing portions, and the actuator remaining wholly contained within the tubular member upon the bending, the method including:
providing the elongate element; and
deforming at least one region of the elongate element in register with the longitudinally extending, continuous, cutaway, bend-enhancing portion of the steering mechanism to inhibit relative rotation of the elongate element and the steering mechanism on bending.

33. The method of claim 32, wherein deforming includes deforming the at least one region of the elongate element by crimping the elongate element.

34. The method of claim 33, wherein crimping includes crimping the elongate element at at least two longitudinally spaced locations on the elongate element.

35. The method of claim 34, wherein crimping includes crimping the elongate element prior to inserting the steering mechanism into the lumen of the elongate element.

36. The method of claim 35, further comprising inserting a former into the lumen of the elongate element prior to crimping the elongate element to limit deformation of the elongate element being crimped.

37. A steering mechanism for a catheter, the steering mechanism including:
   a tubular member defining a passage, the tubular member having a longitudinally extending, continuous, cutaway, bend-enhancing portion formed at a predetermined region of the tubular member to enhance bending at the region; and
   an actuator comprising a tubular element received in the passage of the tubular member, a distal part of the tubular element being fastened to a distal part of the tubular member, a proximal end of the tubular element configured to extend to a handle of the catheter, the actuator being positioned co-axially within the passage of the tubular member, the actuator having a longitudinally extending bend-enhancing portion coincident with the longitudinally extending, continuous, cutaway, bend-enhancing portion of the tubular member, wherein manipulation of the actuator causes bending of the actuator and tubular member at their coincident bend-enhancing portions, the actuator remaining wholly contained within the tubular member at the bend-enhancing portions upon the bending; and
   wherein:
      the tubular member is a first tubular member;
      the actuator is a first actuator, the tubular element of the first actuator received within the passage of the first tubular member; and
      the tubular element of the first actuator defines a second passage and a distal end of one of the tubular member and the tubular element being secured to the other of the tubular member and the tubular element at a termination arranged proximally of a distal end of the other of the tubular member and the tubular element, wherein the mechanism comprises a further actuator received through the passages of the tubular member and the tubular element with a distal part of the further actuator being fastened to a distal part of the other of the tubular member and the tubular element.

38. A steering mechanism for a catheter, the steering mechanism including:
   a tubular member defining a passage, the tubular member having a longitudinally extending, continuous, cutaway, bend-enhancing portion formed at a predetermined region of the tubular member to enhance bending at the region;
   an actuator comprising a tubular element received in the passage of the tubular member, a distal part of the tubular element being fastened to a distal part of the tubular member, a proximal end of the tubular element configured to extend to a handle of the catheter, the actuator being positioned co-axially within the passage of the tubular member, the actuator having a longitudinally extending bend-enhancing portion coincident with the longitudinally extending, continuous, cutaway, bend-enhancing portion of the tubular member, wherein manipulation of the actuator causes bending of the actuator and tubular member at their coincident bend-enhancing portions, the actuator remaining wholly contained within the tubular member at the bend-enhancing portions upon the bending; and
   a series of annular members overlying the longitudinally extending, continuous, cutaway, bend-enhancing portion of the tubular member and over which a protective sheath is received.

39. A steering mechanism for a catheter, the steering mechanism including:
   a tubular member defining a passage, the tubular member having a longitudinally extending, continuous, cutaway, bend-enhancing portion formed at a predetermined region of the tubular member to enhance bending at the region, the longitudinally extending, continuous, cutaway, bend-enhancing portion of the tubular member retaining a longitudinally extending web or spine of material of the tubular member;
   an actuator comprising a tubular element received in the passage of the tubular member, a distal part of the tubular element being fastened to a distal part of the tubular member, a proximal end of the tubular element configured to extend to a handle of the catheter, the actuator being positioned co-axially within the passage of the tubular member, the actuator having a longitudinally extending, continuous, cutaway, bend-enhancing portion coincident with the longitudinally extending, continuous, cutaway, bend-enhancing portion of the tubular member, the longitudinally extending, continuous, cutaway, bend-enhancing portion of the actuator retaining a longitudinally extending web or spine of material of the actuator, wherein the spines of material of the tubular member and the actuator lie in an opposed relationship relative to each other, and manipulation of the actuator causes bending of the actuator and tubular member at their coincident bend-enhancing portions, the actuator remaining wholly contained within the tubular member at the bend-enhancing portions upon the bending;
   an insert arranged between the spines of material of the tubular member and the actuator for controlling bending of the tubular member and the actuator; and
   a protective sheath received over the tubular member and insert to inhibit an ingress of foreign material into the tubular member, wherein a width dimension of the insert imparts a non-circular cross-section to the protective sheath when viewed end-on.

* * * * *

UNITED STATES PATENT AND TRADEMARK OFFICE
CERTIFICATE OF CORRECTION

| | | |
|---|---|---|
| PATENT NO. | : 8,641,697 B2 | Page 1 of 1 |
| APPLICATION NO. | : 11/659274 | |
| DATED | : February 4, 2014 | |
| INVENTOR(S) | : Matthew Partlett et al. | |

It is certified that error appears in the above-identified patent and that said Letters Patent is hereby corrected as shown below:

In the specification:

COLUMN 7, LINE 38, change "respectively a shown" to --respectively, as shown--

In the claims:

CLAIM 22, COLUMN 11, LINE 35, change "of claim 16," to --of claim 21,--
CLAIM 24, COLUMN 11, LINE 65, change "The mechanism of" to --The catheter of--
CLAIM 25, COLUMN 12, LINE 3, change "The mechanism of" to --The catheter of--
CLAIM 26, COLUMN 12, LINE 7, change "The mechanism of" to --The catheter of--

Signed and Sealed this
Twenty-sixth Day of April, 2016

Michelle K. Lee
*Director of the United States Patent and Trademark Office*